(12) United States Patent
Yao et al.

(10) Patent No.: US 6,272,909 B1
(45) Date of Patent: *Aug. 14, 2001

(54) GLIDE HEIGHT TESTING USING A GLIDE HEAD APPARATUS WITH A PIEZOELECTRIC ACTUATOR

(75) Inventors: Wei H. Yao; Ramesh Sundaram, both of Fremont, CA (US)

(73) Assignee: Seagate Technology, LLC, Scotts Valley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/612,790

(22) Filed: Jul. 10, 2000

Related U.S. Application Data

(63) Continuation of application No. 09/252,263, filed on Jan. 18, 1999, now Pat. No. 6,105,421.
(60) Provisional application No. 60/082,232, filed on Apr. 16, 1998.

(51) Int. Cl.[7] ....................................... G01B 5/60
(52) U.S. Cl. ............................................... 73/105
(58) Field of Search ................................ 73/105

(56) References Cited

U.S. PATENT DOCUMENTS

| | | |
|---|---|---|
| 4,624,564 | 11/1986 | Dahlgren . |
| 4,862,029 | 8/1989 | Kasai et al. . |
| 5,021,906 | 6/1991 | Chang et al. . |
| 5,229,951 | 7/1993 | Sugita et al. . |
| 5,293,094 | 3/1994 | Flynn et al. . |
| 5,475,488 | 12/1995 | Fukuzawa et al. . |
| 5,488,857 | 2/1996 | Homma et al. . |
| 5,612,841 | 3/1997 | Johnson . |
| 5,638,234 | 6/1997 | Hagen . |
| 5,701,218 | 12/1997 | Boutaghou . |
| 5,703,684 | 12/1997 | Lu et al. . |
| 5,711,063 | 1/1998 | Budde et al. . |
| 5,757,492 | 5/1998 | Tokutomi et al. . |
| 5,774,305 | 6/1998 | Boutaghou . |
| 5,781,378 | 7/1998 | Heitkamp et al. . |
| 5,796,556 | 8/1998 | Boutaghou . |
| 5,824,920 | 10/1998 | Sugimoto et al. . |
| 5,863,237 | 1/1999 | Felts et al. . |
| 6,088,176 | * 9/2000 | Smith et al. . |
| 6,118,632 | * 9/2000 | Albrecht et al. . |

OTHER PUBLICATIONS

Marchon et al., "Glide Avalanche Prediction From Surface Topography", Transactions of the ASME, vol. 118, Jul. 1996, pp. 644–650.

Kuo et al., "Design of Laser Zone Texture for Low Glide Media", IEEE Transactions on Magnetics, vol. 32, No. 5, Sep. 1996, pp. 3753–3758.

\* cited by examiner

*Primary Examiner*—Robert Raevis
(74) *Attorney, Agent, or Firm*—Fish & Richardson P.C.

(57) ABSTRACT

A glide head apparatus for testing surface characteristics of a disc includes a gimbal, a slider and an actuator including a piezoelectric material disposed between the gimbal and the slider. A voltage applied across the piezoelectric material is controllable to cause the piezoelectric material to expand or contract depending on the applied voltage so as to vary the fly height between the slider and a disc under test. The fly height can be varied without substantially varying the linear velocity of the disc under test. Methods of testing surface characteristics of a disc using the glide head apparatus also are disclosed.

4 Claims, 5 Drawing Sheets

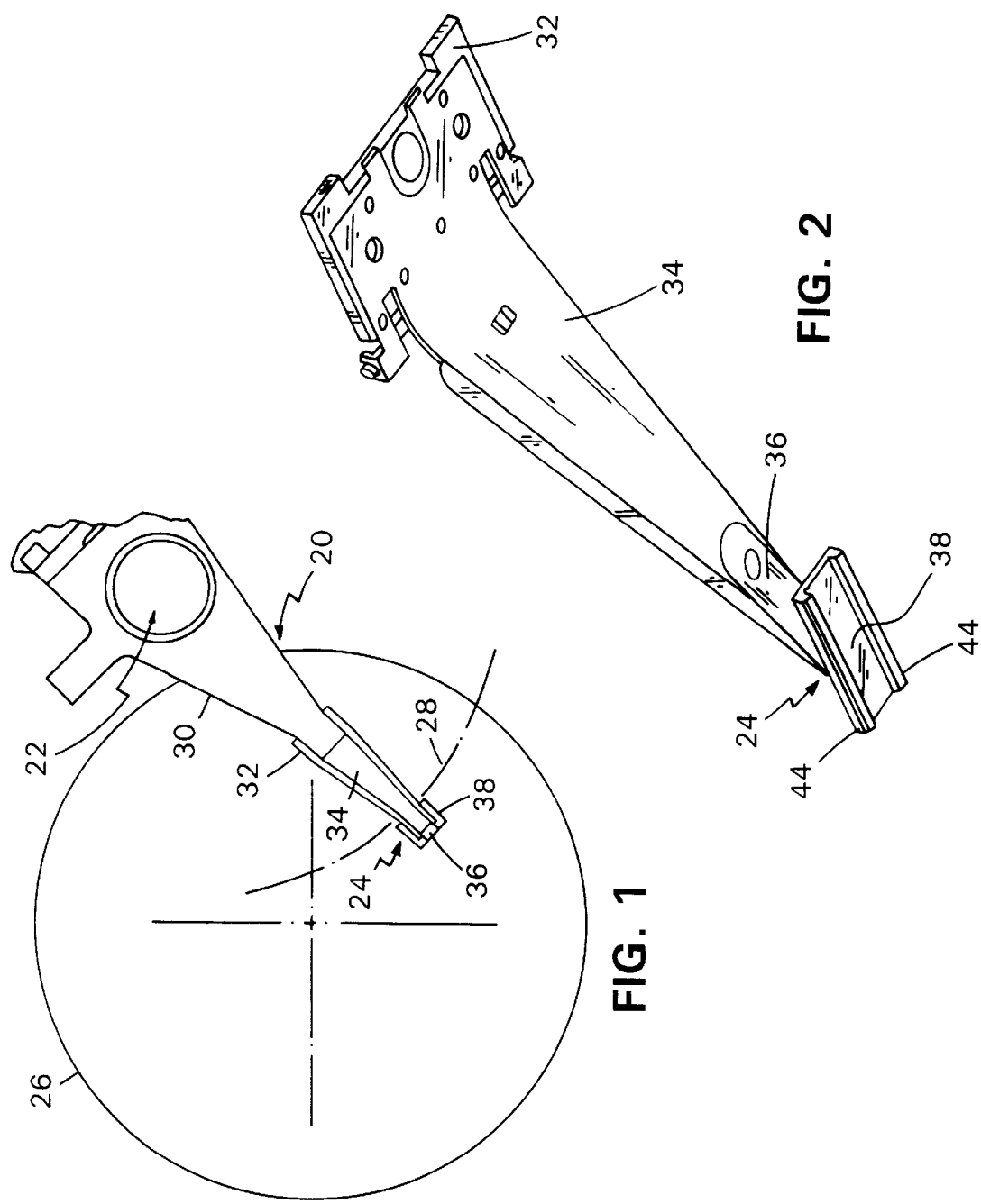

GLIDE HEIGHT TESTING USING A GLIDE HEAD APPARATUS WITH A PIEZOELECTRIC ACTUATOR

CROSS REFERENCE TO RELATED APPLICATIONS

This application is a continuation of U.S. patent application Ser. No. 09/252,263, filed Jan. 18, 1999, now U.S. Pat. No. 6,105,421 which claims the priority of U.S. Provisional Application Serial No. 60/082,232, filed Apr. 16, 1998. This application is related to a concurrently-filed application entitled "Glide Head Apparatus For Testing Recording Media," assigned to the assignee of the present invention and incorporated herein by reference in its entirety.

BACKGROUND

The present invention relates generally to magnetic recording media and, in particular, to apparatus and techniques for testing the glide height characteristics of magnetic recording media.

Disc drives are the primary devices used for mass storage of computer programs and data. Within a disc drive, a load beam supports a hydrodynamic air bearing slider close to a rotating magnetic disc. The load beam supplies a downward force that counteracts the hydrodynamic lifting force developed by the slider's air bearing. During operation, the magnetic head rides at a distance from the surface of the magnetic disc. That distance must be small enough to allow high density recording while preventing damage that would otherwise be caused by contact between the spinning disc and the magnetic head.

High areal densities currently are achieved by reducing the separation between the disc and the head to less than twenty nanometers (nm). However, some level of disc roughness is required to reduce adhesive forces when the head is at rest. The level of disc surface topography must, therefore, be kept within a tight range to fly the head safely at low altitudes while simultaneously preventing it from sticking to the disc surface when the head is at rest. Thus, the topography of the disc surface is critical to the proper operation of the disc drive.

As part of the process of manufacturing hard files, the quality of a magnetic disc is provided by determining the glide conditions which can be established between the disc and a glide head. In particular, the effect of outwardly projecting defects on the surface of the magnetic disc is studied during glide height testing. When such defects are large enough to close the gap between the magnetic disc and the glide head, the defects strike the glide head. The movement of the glide head can be sensed, for example, by a sensor such as a piezoelectric transducer, which generates an electrical signal indicating the adjacent passage of an outwardly projecting defect.

During testing, a gliding action is brought about as a layer of air, dragged along by the spinning disc surface, is compressed between the surface of the disc and the adjacent surface of the glide head. As a result of the gliding action, the glide head rides at a distance from the surface of the disc. That distance is referred to as the "fly" height of the glide head and is determined, in part, by the peripheral speed of the rotating disc and the air pressure surrounding the disc. Thus, the fly height of the glide disc can be varied by changing the speed at which the disc rotates. A glide avalanche breaking point (GABP), which is used by engineers to characterize the surface of the disc, can be obtained based on the interaction between the disc surface and the glide head at different fly heights.

Several difficulties arise, however, when the linear velocity of the disc is varied to obtain a measure of the glide avalanche breaking point. The impact energy which is detected by a sensor depends on the velocity and, in some cases, is approximately proportional to the square of the velocity. Thus, it can be difficult to interpret the signals received by such a sensor. Furthermore, changing the linear velocity can affect the pitch and roll of the glide head. That, in turn, can affect the level of interference detected by the sensor. Additionally, the relationship between fly height and linear velocity may not be linear at very low speeds, such as speeds less than 200 inches per second, making it difficult to correlate the velocity with fly height.

SUMMARY

In general, glide head apparatus and methods for testing surface characteristics of a disc, such as a magnetic disc, are disclosed. The techniques can be used, for example, to perform glide tests in which the fly height is varied while the linear velocity of the disc remains substantially constant.

According to one aspect, the glide head apparatus includes a gimbal, a slider and an actuator including a piezoelectric material disposed between the gimbal and the slider. A voltage applied across the piezoelectric material is controllable to cause the piezoelectric material to expand or contract depending on the applied voltage so as to vary a distance, such as the fly height, between the slider and a disc under test.

Various implementations include one or more of the following features. The voltage across the piezoelectric material can be controlled by a digital signal processor. The voltage applied across the piezoelectric material can be controlled to vary the fly height of the glide head apparatus without substantially varying the linear velocity of the disc under test. In some cases, the piezoelectric material is expandable over a range of at least about 0.010 inch.

The piezoelectric material can comprise a ferroelectric material, such as lead zirconium titanate. Other piezoelectric materials also can be used. In some implementations, multiple piezoelectric actuators are coupled in series. The voltages across the respective piezoelectric actuators can be controlled to provide a corresponding change in the fly height of the glide head apparatus.

In some embodiments, the glide head apparatus also includes an arm with a load arm, and an actuator for positioning the arm over the disc. The gimbal can be attached to the load arm. The apparatus also can include a transducer for sensing interactions between the slider and the disc under test.

According to another aspect, a method of testing surface characteristics of a disc includes causing the disc to rotate at a predetermined linear velocity with a glide head positioned at an initial fly height above a surface of the disc. The method further includes acquiring data indicative of interactions between the glide head and the disc while the disc is rotating at the predetermined linear velocity. The voltage across a piezoelectric actuator is changed to cause a corresponding change in the fly height between the glide head and the surface of the disc. The act of acquiring data can be repeated once the fly height has been changed.

One or more of the following features are present in some implementations. The act of changing the voltage across the piezoelectric actuator can cause a reduction in the fly height. Furthermore, the acts of changing the voltage and acquiring data indicative of interactions between the glide head and the disc can be repeated until sufficient information is acquired to determine a glide avalanche breaking point for the disc. Acquiring data at different fly heights can be performed while the disc rotates at a substantially constant linear velocity. The acquired data can be used to determine whether the disc passes the glide test.

Various embodiments include one or more of the following advantages. Using a substantially constant linear velocity as the fly height is varied during the glide test makes it easier to interpret the signals indicative of the interaction between the glide head and the disc. For example, the effect of unknown variables, such as the effect the velocity has on the impact energy between the disc and the glide head, can be removed or reduced. Additionally, using a substantially constant linear velocity can reduce the effects on the pitch and roll of the glide head that a changing velocity may cause.

Other features and advantages will be readily apparent from the following detailed description, the accompanying drawings, and the claims.

BRIEF DESCRIPTION OF THE DRAWINGS

FIG. 1 is a plan view of a load arm supporting a head gimbal assembly embodying the present invention.

FIG. 2 is a perspective view of the load arm and head gimbal assembly of FIG. 1.

DETAILED DESCRIPTION

Figure 3:
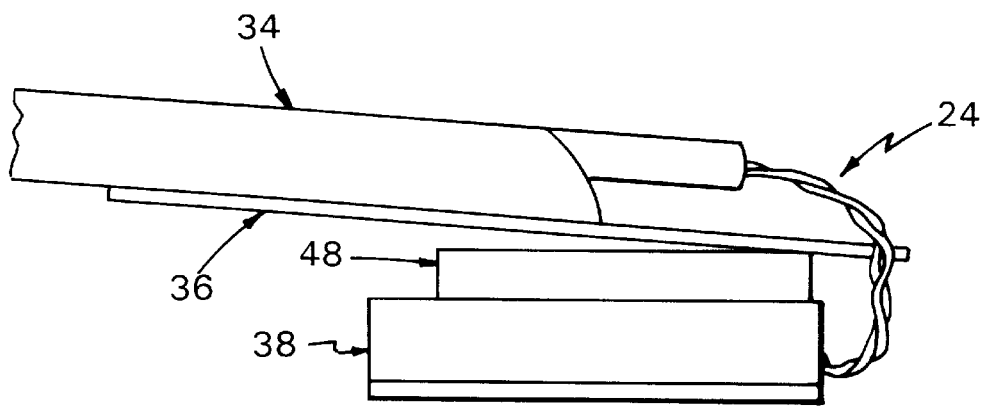
FIG. 3 is a simplified side view of the head gimbal assembly including a piezoelectric actuator according to the invention.

Referring to FIGS. 1 and 2, a glide head assembly includes an actuator arm 20 connected to an actuator 22 and supports a head gimbal assembly (HGA) 24 over a magnetic disc 26. The actuator 22 positions the arm 20 along an arc 28 over the magnetic disc 26. The arm 20 includes a supporting arm 30, a base plate 32, and a load arm 34. The HGA or glide head 24 includes a gimbal 36 and a slider 38. The actuator 22 rotates the arm 20 to position the slider 38 along the arc 28.

The gimbal 36 is welded to the load arm 34 and resiliently supports the slider 38 and allows it to pitch and roll while it follows the topography of the rotating disc 26. The slider 38 includes a self-acting hydrodynamic air bearing surface which can take the form of multiple rails 44 with tapered forward surfaces. The rotating disc 26 forces air into the tapers and produces pressure beneath the rails 44 resulting in the air bearing surface.

The load arm 34 is compliant in the vertical axis to allow the slider 38 to follow the topology of the disc 26, and is rigid in the in-plane axes for precise positioning of the slider. The load arm 34 also supplies a downward force that counteracts the hydrodynamic lifting force developed by the slider's air bearing.

Figure 4:
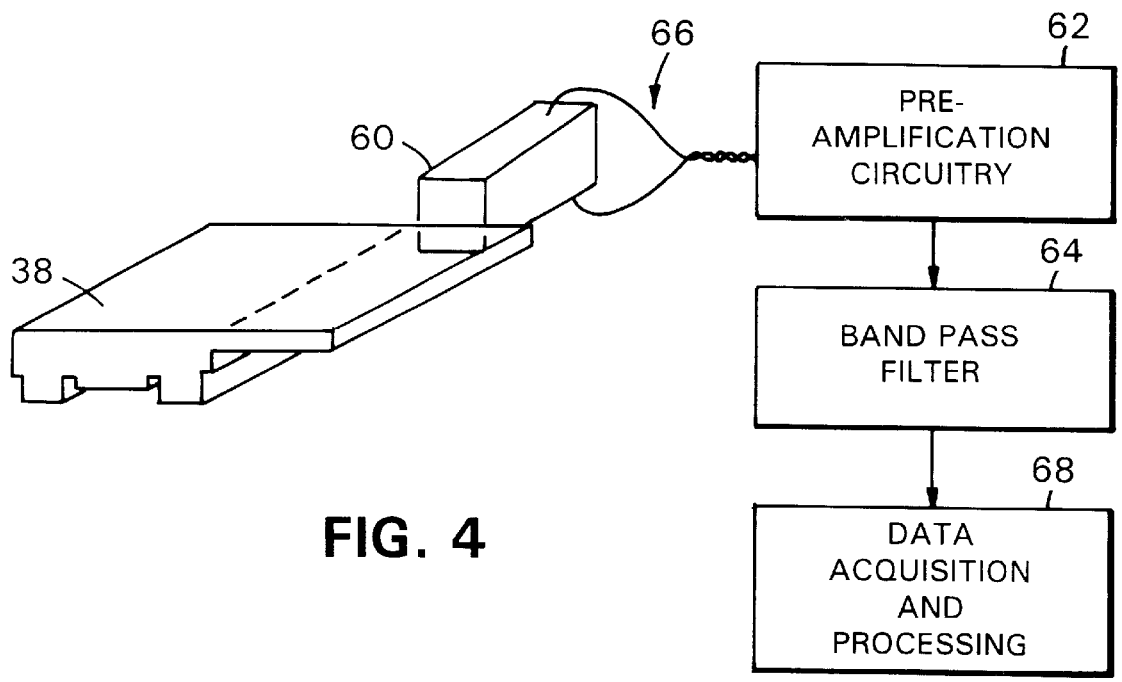
FIG. 4 is a partial side view illustrating additional details of the head gimbal assembly.

During the glide test process, if contact occurs between the glide head 24 and a disc asperity or a defect, the glide head vibrates and is deformed slightly. The deformation of the slider 38 results in deformation of a piezoelectric transducer 60 (FIG. 4) which can be mounted on an extended wing of the trailing edge of the slider 38. A potential difference is generated between the electrodes of the transducer, and the transducer generates an electrical signal indicating that the glide head has struck the surface of the rotating disc 10. Electric signals generated by the transducer are provided to pre-amplification circuitry 62 and a band pass filter 64 via small twisted copper wires 66. A digital data acquisition system 68 processes the filtered data to compute the GABP and to determine whether the disc passes or fails the glide test.

The glide head assembly 18 also includes a piezo-electric actuator 48 disposed between the gimbal 36 and the slider 38 (FIG. 3). The piezoelectric actuator 48 can be attached to the gimbal 36 and the slider 38 using, for example, an epoxy glue. In one implementation, the piezo-electric actuator 48 comprises a ferroelectric material such as lead zirconium titanate ($PbZrTi_3$), also known as PZT.

The crystal structure of PZT contains inherent asymmetries in its lattice. In general, a material comprising PZT can be deposited on a wafer to a thickness on the order of one micron, for example, by a sol gel process. The PZT material then is annealed at a high temperature to form a crystalline lattice. Finally, the PZT material is poled to induce the desired piezoelectric properties. In other words, the random polarized crystal orientations in the ceramic are permanently aligned by application of a strong electric field. Once the material is poled, the PZT film will expand piezoelectrically when a voltage of one polarity is applied across it and will contract when a voltage of the opposite polarity is applied. Other piezoelectric materials also can be used for the actuator 48, including, for example, $PbTiO_3$ and $PbZrO_3$.

With respect to the piezoelectric actuator 48, one electrode can be attached to the underside of the slider 36 which can comprise a conductive material. The backside surface of the actuator 48 is slightly larger than the gimbal 38 so that a second electrode can be attached to the backside surface. When a voltage of a first polarity, for example, a negative voltage, is applied, the actuator expands so that the glide head moves closer to the surface of the disc 26. On the other hand, when a voltage of the opposite polarity, for example, a positive voltage, is applied, the actuator 48 contracts so that the glide head moves away from the surface of the disc 26. Thus, by controlling the voltage applied to the piezoelectric actuator 48, the vertical position of the slider 38 can be controlled precisely. In general, the expansion or contraction of the piezoelectric actuator 48 and, therefore, the displacement of the slider 38 in the vertical direction corresponds to the applied voltage. In this way, the fly height of the glide head over the surface of the disc 26 can be varied without changing the rotational speed of the disc.

The range of variation in the contraction and expansion of the piezoelectric actuator 48 should be at least about 10 to about 20 percent of the "Z-height" which refers to the vertical distance from the base of the mounting plate 32 to the upper surface of the disc 26. For example, if the Z-height is approximately 100 mils (0.100 inch), the actuator 48 should be capable of contracting and/or expanding over a range of at least about 10 to 20 mils (0.010 to 0.020 inch).

Figure 5:
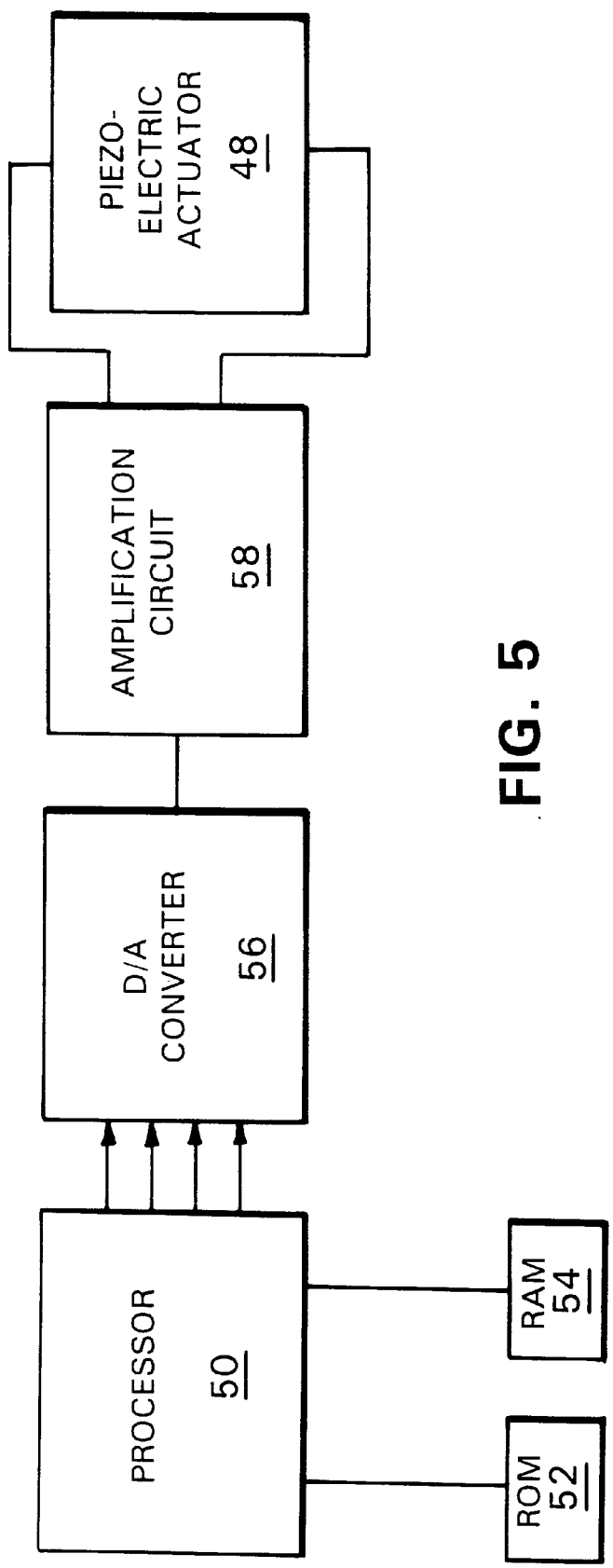
FIG. 5 is a block diagram illustrating a control system for the piezoelectric actuator.
Figure 6:
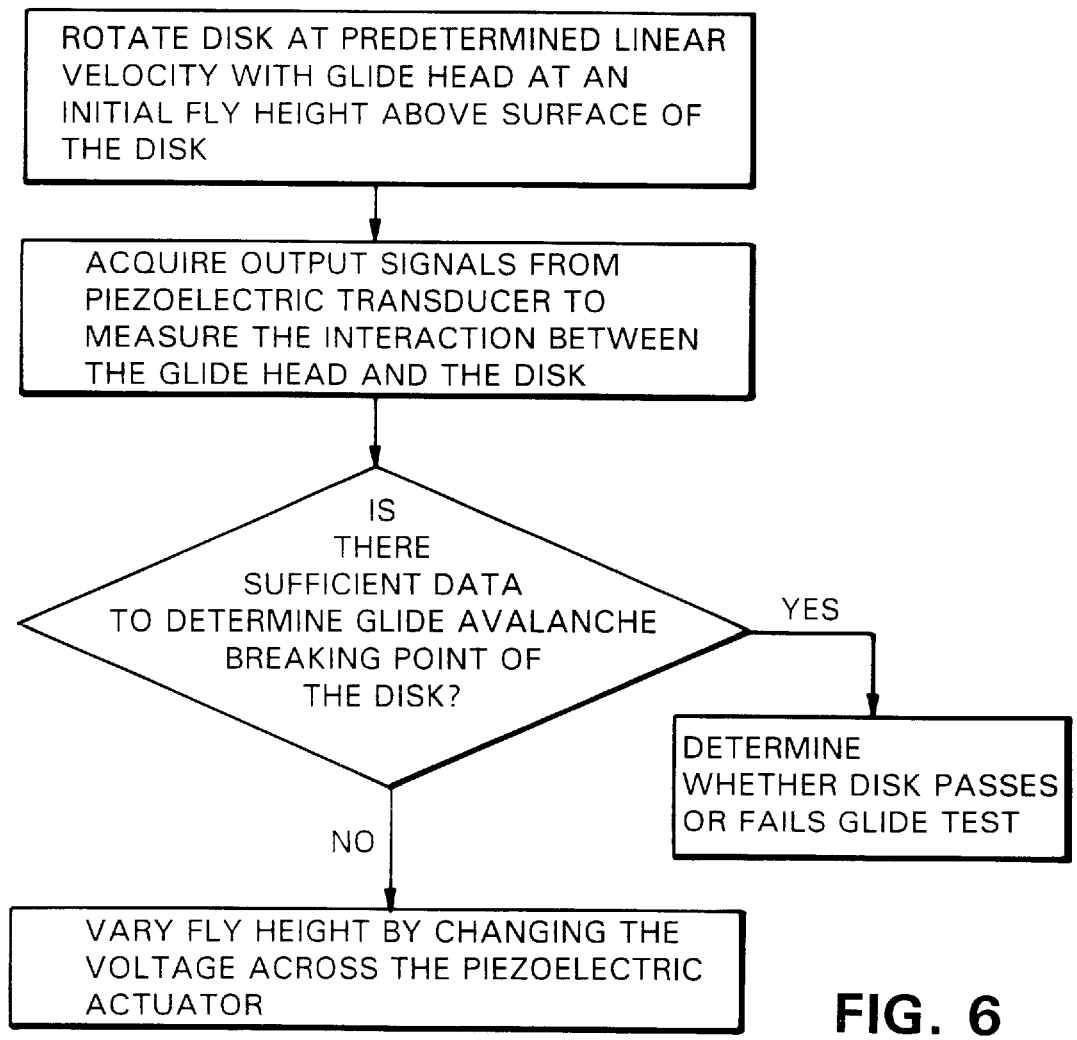
FIG. 6 is a flow chart of a method according to the invention.

Referring to FIG. 5, a processor 50, such as a programmable digital signal processor (DSP), is programmed to control the operation of the piezoelectric actuator 48. Alternatively, the processor 50 can include a central processing unit, a general purpose or special purpose processor, a minicontroller, a microprocessor or a microcomputer for controlling operation of the piezoelectric actuator 48. Various types of memory are associated with the processor 50, including read only memory (ROM) 52 and random access memory (RAM) 54. The processor 50 provides output signals which are representative of the magnitude and polarity of the voltage to be applied to the piezoelectric actuator 48. Those signals are provided to a digital-to-analog (D/A) converter 56. The output of the D/A converter 56 is provided to an amplifying circuit 58. The amplifying circuit 58 then provides a voltage which is applied across the piezoelectric actuator 48.

In operation, a disc 26 under test is rotated at a predetermined linear velocity so that the slider glide head is positioned at an initial fly height $h_1$ above the surface of the disc 26. The linear velocity of the disc 26 can be selected to coincide approximately with the expected GABP of the disc. For example, for a sample disc having a GABP of about 1.0 micro-inch, a glide write 11-mil head having a fly height of about 1.0 micro-inch can be used, with the disc 26 spinning at a linear velocity of about 400 inches per second. Output signals from the piezoelectric transducer are obtained at the initial fly height $h_1$. The voltage across the PZT actuator 48 then is adjusted to cause the actuator to expand in the vertical direction by a predetermined amount. As the actuator 48 expands in the vertical direction, the slider 38 is brought closer to the surface of the disc 26 by a corresponding amount. The linear velocity of the disc 26, however, remains substantially constant. Again, output signals from the transducer are obtained which correspond to a second fly height $h_2$. The process is repeated such that the fly height of the HGA 24 is changed by varying the voltage across the PZT actuator 48, and the interaction between the GHA and the disc 26 is sensed by the transducer. The process is continued until sufficient data has been collected to determine the glide avalanche breaking point of the disc 26 or until the fly height reaches a predetermined minimum value.

The linear velocity of the disc 26 can remain substantially constant even as the fly height of the GHA 24 is varied. Using a substantially constant linear velocity as the fly height is varied during a glide test makes it easier to interpret signals from the transducer 60 by removing certain unknown variables such as the effect that the velocity has on the impact energy between the disc 26 and the slider 38. Additionally, using a substantially constant linear velocity can reduce the effects on the pitch and roll of the glide head that a changing velocity may cause.

Figure 7:
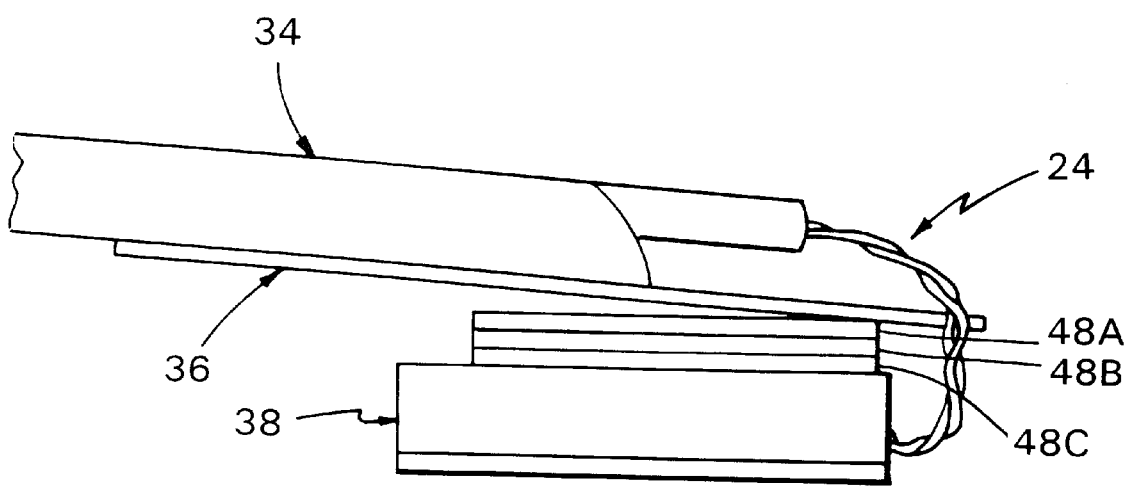
FIG. 7 illustrates another embodiment of the head gimbal assembly with multiple piezoelectric actuator in series according to the invention.

Although the embodiment discussed above incorporates a single piezoelectric actuator 48, in other implementations two or more piezoelectric actuators 48A, 48B and 48C (FIG. 7) can be provided in series between the gimbal 36 and the slider 38. By controlling the voltage applied across each of the piezoelectric material in each of the actuators 48A, the actuators either expand or contract by a desired amount, thereby changing the fly height of the glide head.

Other implementations are within the scope of the following claims.

What is claimed is:

1. A glide head apparatus comprising:

a glide head; and means for controllably adjusting the fly height of the glide head with respect to a disc under test without substantially varying a linear velocity of the disc under test, wherein the means for controllably adjusting the fly height includes:

a plurality of piezoelectric actuators; and a processor configured to provide output signals representative of the magnitude and polarity of voltages applied to the piezoelectric actuators.

2. The apparatus of claim 1 wherein the means for controllably adjusting the fly height includes:

a digital-to-analog converter coupled to receive the output signals from the processor; and an amplifying circuit coupled to receive an output from the digital-to-analog converter and configured to apply the voltages to the piezoelectric actuators.

3. The apparatus of claim 2 wherein the processor comprises a programmable digital signal processor.

4. The apparatus of claim 1 wherein the piezoelectric actuators are arranged in series.

* * * * *